(12) United States Patent
Karkowski

(10) Patent No.: US 9,928,715 B2
(45) Date of Patent: Mar. 27, 2018

(54) SYSTEM FOR IDENTIFYING A CHANGE IN WALKING SPEED OF A PERSON

(71) Applicant: Dutch Domotics B.V., Rotterdam (NL)

(72) Inventor: Ireneusz Piotr Karkowski, Delft (NL)

(73) Assignee: Dutch Domotics B.V., Rotterdam (NL)

( * ) Notice: Subject to any disclaimer, the term of this patent is extended or adjusted under 35 U.S.C. 154(b) by 0 days.

(21) Appl. No.: 15/325,617

(22) PCT Filed: Jul. 30, 2015

(86) PCT No.: PCT/EP2015/067453
§ 371 (c)(1),
(2) Date: Jan. 11, 2017

(87) PCT Pub. No.: WO2016/020247
PCT Pub. Date: Feb. 11, 2016

(65) Prior Publication Data
US 2017/0162021 A1 Jun. 8, 2017

(30) Foreign Application Priority Data
Aug. 6, 2014 (EP) ..................................... 14180032

(51) Int. Cl.
*G08B 23/00* (2006.01)
*G08B 21/04* (2006.01)
(Continued)

(52) U.S. Cl.
CPC ........ *G08B 21/0423* (2013.01); *A61B 5/1113* (2013.01); *A61B 5/6889* (2013.01);
(Continued)

(58) Field of Classification Search
CPC .... A61B 5/1113; A61B 5/1115; A61B 5/1118; A61B 5/002; A61B 5/0002; A61B 5/0022; A61B 2503/08; A61B 5/6889; G08B 21/04; G08B 21/06; G08B 21/0423; G08B 21/0438; G08B 21/0469; G08B 21/0476; G08B 21/0492
(Continued)

(56) References Cited

U.S. PATENT DOCUMENTS

| 7,535,368 B2 | 5/2009 | Graichen et al. |
| 2006/0058704 A1 | 3/2006 | Graichen et al. |

(Continued)

FOREIGN PATENT DOCUMENTS

JP 2004-164282 A 6/2004

*Primary Examiner* — Thomas Mullen
(74) *Attorney, Agent, or Firm* — Richard M. Goldberg

(57) ABSTRACT

A system for identifying a change in walking speed of a person includes plurality of sensors (8,9,10,11,18) disposed among a plurality of locations in a living space (20). Each of the plurality of sensors (8,9,10,11,18) is operable to detect one of motion of the person or location of the person. Travel times (tt) for a path (19) traveled by the person through the living space (20) are measured based on the signals of the plurality of sensors (8,9,10,11,18). A reliability indication (R1) of the likelihood that another person is visiting the living space (20) is established. A change in the person's walking speed is identified by identifying changes in the travel times (tt), disregarding travel times (tt) which are indicated as unreliable by the reliability indication (R1).

11 Claims, 7 Drawing Sheets

| Date | hour | travel time (sec) | RI |
|---|---|---|---|
| 03/04/14 | 8:45 | 11 | Y |
| 03/04/14 | 12:05 | 10 | Y |
| 03/04/14 | 19:55 | 9 | Y |
| 03/04/14 | 22:36 | 10 | Y |
| 03/05/14 | 8:30 | 10 | Y |
| 03/05/14 | 13:47 | 9 | Y |
| 03/05/14 | 22:57 | 27 | N |
| 03/06/14 | 8:23 | 11 | Y |
| 03/06/14 | 13:12 | 10 | Y |
| 03/06/14 | 17:44 | 11 | Y |
| 03/06/14 | 23:09 | 11 | Y |
| 03/07/14 | 8:27 | 10 | N |
| 03/07/14 | 10:00 | 8 | N |
| 03/07/14 | 13:09 | 9 | N |
| 03/07/14 | 14:23 | 9 | N |
| 03/07/14 | 14:30 | 12 | N |
| 03/07/14 | 15:09 | 11 | N |
| 03/07/14 | 17:08 | 10 | N |
| 03/07/14 | 18:34 | 11 | N |
| 03/07/14 | 18:41 | 8 | N |
| 03/07/14 | 22:09 | 11 | N |
| 03/08/14 | 8:46 | 10 | Y |
| 03/08/14 | 11:42 | 11 | Y |
| 03/08/14 | 17:43 | 9 | Y |
| 03/08/14 | 21:57 | 11 | Y |

(51) Int. Cl.
*A61B 5/11* (2006.01)
*A61B 5/00* (2006.01)

(52) U.S. Cl.
CPC ..... *G08B 21/0469* (2013.01); *G08B 21/0476* (2013.01); *G08B 21/0492* (2013.01); *A61B 2503/08* (2013.01); *A61B 2505/07* (2013.01)

(58) Field of Classification Search
USPC ........................ 340/573.1, 573.4, 545.1, 523
See application file for complete search history.

(56) References Cited

U.S. PATENT DOCUMENTS

| | | |
|---|---|---|
| 2006/0267780 A1 | 11/2006 | Adams |
| 2009/0051524 A1* | 2/2009 | Lim .................. A61B 5/00 340/501 |
| 2011/0153545 A1 | 6/2011 | Greene et al. |
| 2013/0141233 A1* | 6/2013 | Jacobs ................ G08B 19/00 340/521 |

* cited by examiner

| Date | hour | travel time (sec) | RI |
|---|---|---|---|
| 03/04/14 | 8:45 | 11 | Y |
| 03/04/14 | 12:05 | 10 | Y |
| 03/04/14 | 19:55 | 9 | Y |
| 03/04/14 | 22:36 | 10 | Y |
| 03/05/14 | 8:30 | 10 | Y |
| 03/05/14 | 13:47 | 9 | Y |
| 03/05/14 | 22:57 | 27 | N |
| 03/06/14 | 8:23 | 11 | Y |
| 03/06/14 | 13:12 | 10 | Y |
| 03/06/14 | 17:44 | 11 | Y |
| 03/06/14 | 23:09 | 11 | Y |
| 03/07/14 | 8:27 | 10 | N |
| 03/07/14 | 10:00 | 8 | N |
| 03/07/14 | 13:09 | 9 | N |
| 03/07/14 | 14:23 | 9 | N |
| 03/07/14 | 14:30 | 12 | N |
| 03/07/14 | 15:09 | 11 | N |
| 03/07/14 | 17:08 | 10 | N |
| 03/07/14 | 18:34 | 11 | N |
| 03/07/14 | 18:41 | 8 | N |
| 03/07/14 | 22:09 | 11 | N |
| 03/08/14 | 8:46 | 10 | Y |
| 03/08/14 | 11:42 | 11 | Y |
| 03/08/14 | 17:43 | 9 | Y |
| 03/08/14 | 21:57 | 11 | Y |

Fig. 4

SYSTEM FOR IDENTIFYING A CHANGE IN WALKING SPEED OF A PERSON

FIELD OF THE INVENTION

The invention relates to a system for identifying a change in walking speed of a person on the basis of a changing in travel times measured when the person walks along a known path in his living space.

BACKGROUND OF THE INVENTION

Many elderly people live alone. The elderly also are at risk from disease and illness. Among other symptoms, a person may begin walking slower as their health declines or when they become ill. Similarly, a person recovering from an illness may begin walking faster as their health improves. Thus, a person's walking speed may be used as an indicator of health.

A system for identifying the walking speed of person in his living space is disclosed in U.S. Pat. No. 7,535,368.

The disclosed system comprises a plurality of sensors disposed in various rooms of a home. The sensors provide signals representative of motion and/or the location of the person within the home. The system also includes a unit receiving the sensor signals. The unit derives the location of the person on the basis of the sensor signals. The unit establishes a travel time for a path traveled by the person through the structure based on the established locations and stores the travel time. The unit measures the time traveled by the person through his home along a path defined by a number of sensor locations. The unit identifies a change in the person's walking speed by identifying changes in the travel time for the path traveled by the person.

The system may alert a caregiver to inform them of the change in walking speed identified by the system.

It is important that the reliability of the determined changing in walking speed is high, so that the caregiver can trust the information about the walking speed changings and false alerts are prevented.

SUMMARY OF INVENTION

It is an object of the invention to provide a system, which determines the changing of the walking speed with an improved reliability.

This object is achieved by a system for identifying a change in walking speed of a person, the system comprising: a plurality of sensors to be disposed among a plurality of locations in a living space, wherein each of the plurality of sensors is operable to detect one of motion of the person or location of the person, means to establish a travel time for a path traveled by the person through the living space based on the signals of the plurality of sensors and to store the travel time, means to establish a reliability indication of the likelihood that another person is visiting the living space, and means to identify a change in the person's walking speed by identifying changes in the travel time for the path traveled by the person through the living space, disregarding travel times which are indicated as unreliable by the reliability indication.

The invention is at least partly based on the insight that visitors can substantially disturb the measurements of the travel times. By determining the presence of a visitor and disregarding the measurements of the walking times in the period that the presence of the visitor is detected a substantial improvement of the reliability of the measurements of the travel times and consequently also a substantial improvement of the reliability of the identification of changings in walking speed is achieved.

In an embodiment of the invention the system is operable to establish event signals from the signals received from said sensors and/or additional signals received from additional sensors detecting a status and/or activities of persons in the living space, which event signals are indicative for events caused by persons in the living space, wherein the reliability indication is dependent on a number of established events in an observation period in which the related travel time (tt) is established.

In case a further person is visiting the living space, this will result in an increase of a number of detected events. So the presence of the further person can be easily and in cost-effective manner determined.

In an embodiment of the system according to the invention only two detectors are used for establishing the travel speed, a first one of two sensors is a sensor for detecting the presence of the person in the bathroom or toilet and a second one of two sensors is a sensor for detecting the presence of the person in another room.

It appears that the persons visiting the toilet usually use the same path. They seldom make a detour. So the travel time between leaving the toilet and entering a room is a reliable indication of the travel time.

BRIEF DESCRIPTION OF THE DRAWINGS

These and other aspects of the invention will be apparent from and elucidated further with reference to the embodiments described by way of example in the following description and with reference to the accompanying drawings, in which FIG. 4 shows an exemplary format for a list comprising the determined travel times for use in an embodiment of the system according to the invention.

DETAILED DESCRIPTION OF EMBODIMENTS

In the subsequent paragraphs, various aspects of a technique for unobtrusively measuring the walking speed of a person in their own home and for identifying a change in the person's walking speed will be explained.

Figure 1:
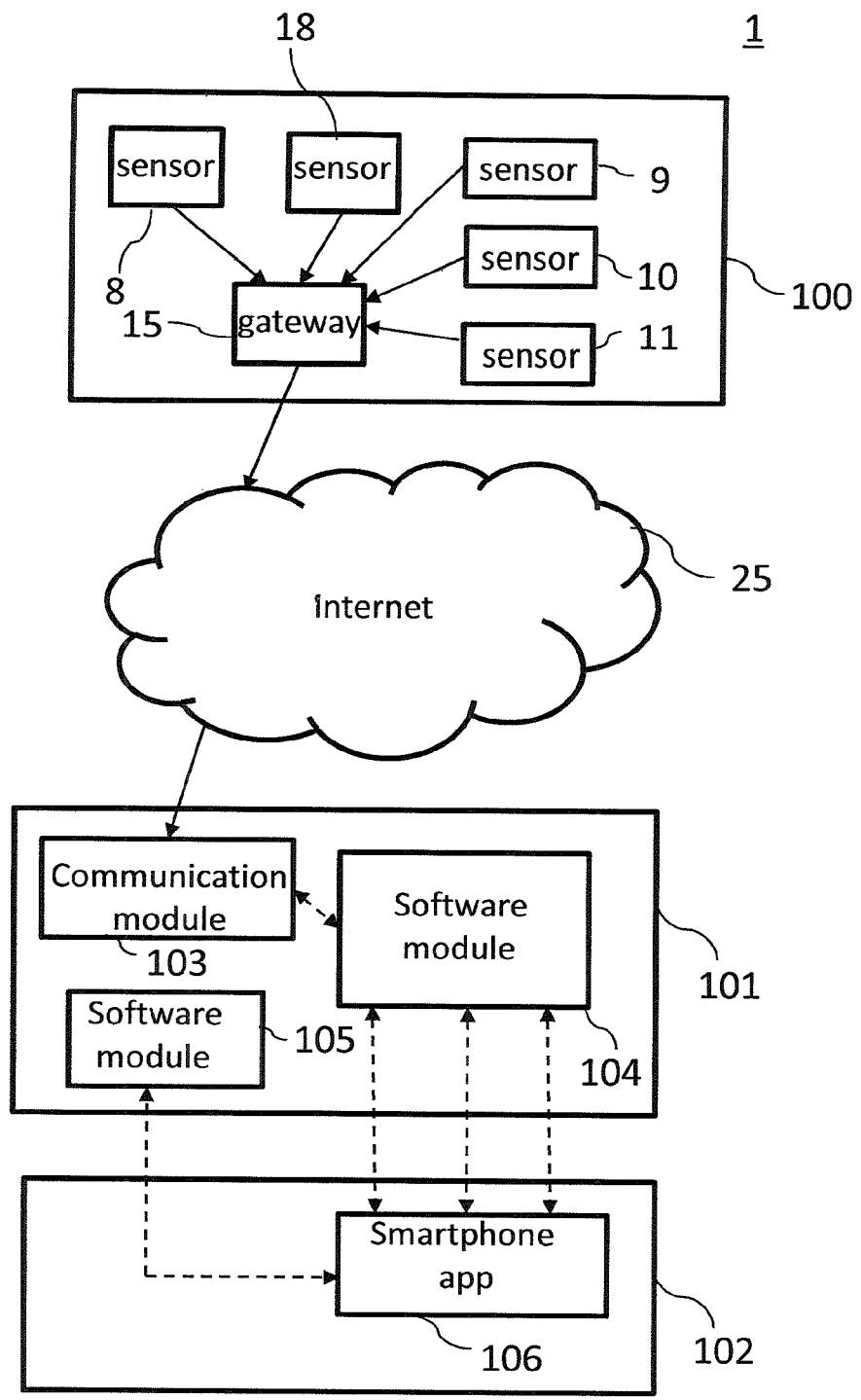
FIG. 1 shows an embodiment of an unattended autonomous surveillance.

FIG. 1 shows an embodiment of a lifestyle monitoring system 1 for monitoring for example, elderly residents in their own house or in a nursery house. The system 1 comprises three major groups of components, indicated by reference signs 100, 101 and 102 respectively.

Group 100 is a group of components placed in a living space of a person to be monitored. It forms a sensor network comprising a plurality of sensors 8, 9, 10, 11, and 18. Sensors 9, 10 and 11 comprise detectors, actuated by opening or closing a door or drawer. These detectors can for example be switches, accelerometer-based sensors or any other detector which can detect the opening and closing of a door or drawer. Sensors 8 and 18 comprise motion sensors. The network is connected to Internet 25 via a gateway 15 of a usual type, e.g. a Zigbee gateway. The gateway 15 receives sensor signals generated by the sensors 8,9,10,11 and 18 and outputs a data signal representing the sensor signals to the Internet 25.

Group 101 forms a processor-controlled system, for example an Internet server. Group 101 comprises a communication module 103 also connected to the Internet 25 for receiving the data signal and extracting the sensor signals from the data signal. The monitoring functionality and functionality for detection of behavior deviation and notification of detected deviation is implemented in a software module 104. The software module 104 is combined with another software module 105 software for user management and scalability. All software runs on the processor-controlled system.

Group 102 comprises a message receiving device, for example a smartphone provided with a so-called smartphone app 106. The smartphone app 106 is coupled with group 101 via a mobile phone/data network. The smartphone app 106 can be used by a caregiver or family member to install and configure the system, to inspect trends in the behavior of the elderly persons and to receive notifications/alerts about detected (mild or severe) deviations in their usual behavior.

In operation the software module 104 analyses the signals of the sensors 8, 9, 10, 11 and 18 and automatically detects deviations from the usual behavior or other deviations, which could be indicative of an emergency. The family of the elderly person or caregiver is notified/alerted via the smartphone app 106 if a deviation occurs which exceeds a predetermined threshold. This gives the caregiver or family member an opportunity to verify the situation (i.e. by phone).

After that, depending on the nature of the deviation (mild or severe), they can take care that a suitable medical intervention is implemented or can involve appropriate emergency services.

Figure 2:
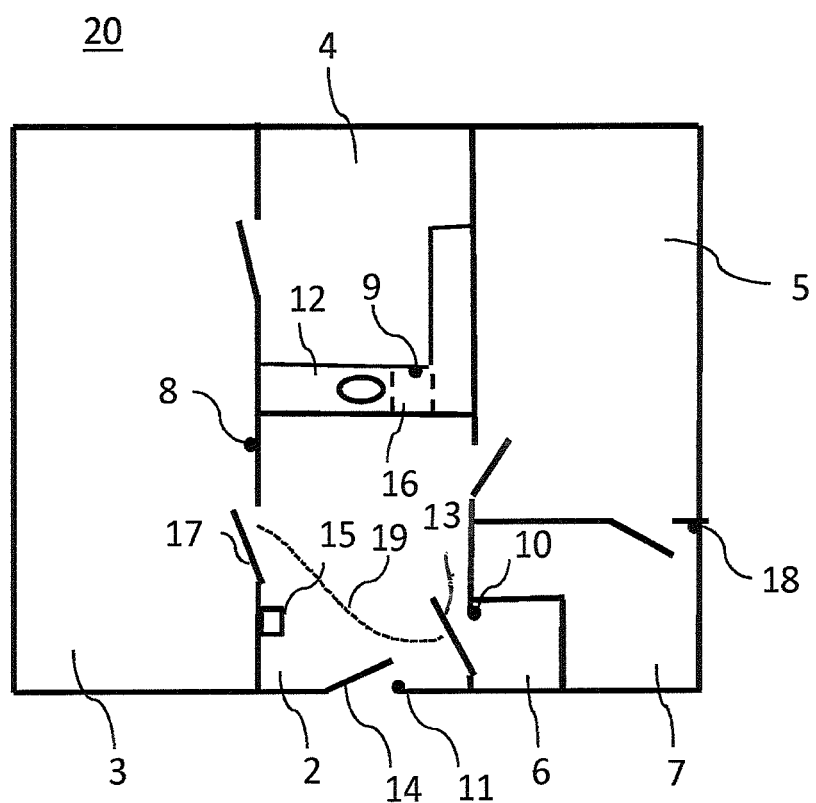
FIG. 2 shows a map of a living space.

FIG. 2 shows a map of a living space 20, in the form of a typical apartment for elderly persons. The apartment comprises a hall 2, a living room 3, a kitchen 4, a bedroom 5, a bathroom 7 and a toilet 6.

The sensors 8, 9, 10 11 and 18 are installed for detecting the presence and/or activity of a person in the living space 20. The motion sensor 8 is located in the living room 3 for detecting the presence of a person in the living room 3. The motion detector 18 is located in the bathroom 7 for detecting the presence of a person in the bathroom 7. The sensor 9 is a detector fixed to a drawer 16 for the utensils in a kitchen counter 12 in the kitchen 4 for detecting the opening and closing of the drawer 16. The sensor 10 is a door detector for detecting the opening and closing of a door 13 of the toilet 6. Sensor 11 is a door detector for detecting the opening and closing of an outside door 14. The gateway 15 is located in the hall 2. The sensors 8, 9, 10, 11 and 18 are coupled to the gateway 15 to submit sensor signals to the gateway 15. This coupling is preferably a wireless connection, but alternatively a wired connection can be used.

The program module 104 comprises a subprogram of a usual type to derive events E1, . . . , E10 from the sensor signals. These events indicate activities caused by the person in the living space 20. Event E1, indicating that a person is leaving the living room 3 and event E2, indicating that a person is entering the living room 3, are derived from the sensor signal provided by motion sensor 8 in the living room 3. Event E3, indicating the opening of the drawer 16, and event E4 indicating that the drawer 16 is closed are derived from the signal provided by sensor 9. Event E5 indicating that a person opens the door 13 of the toilet 6 and event E6 indicating that the person closes the toilet door 13 are derived from the sensor signals provided by sensor 10. Event E7, indicating that a person is leaving the bathroom 7, and event E8, indicating that a person is entering the bathroom 7, are derived from the sensor signal provided by motion sensor 18 in the bathroom 7. Event E9 indicates that outside door 14 is opened and event E10 indicates that the outside door 14 is closed. Events E9 and E10 are derived from the detector 11.

In the embodiment described above two motion sensors and three door/drawer detectors are used as basis for the detection of the events. It will be clear that the number of detectors can vary. More or fewer detectors can be used in the sensor network.

Also, other types of sensors may be used, for example a sensor which detects that an apparatus or lamp is switched on and/or off or a sensor which detects whether a telephone call is made. Also, a camera in combination with an image analyzer can be used to detect the presence or activity of a person.

The software module 104 comprises a program which derives from the events a walking speed and changes in the walking speed of the person living in the living space 20. A decrease in walking speed is often a symptom that the health condition declines or that the person is becoming ill. Similarly, a person recovering from an illness may begin walking faster as their health improves. Thus, a person's walking speed may be used as an indicator of the health of the person.

The walking speed can be determined by measuring the time that it takes for the person to walk a distance between two known locations. The events E1 to E8 all indicate a position of the person at the moment that the event is detected. So, measuring the time difference between two different events provides information about the walking speed, assuming that the person is walking along a known path between these two locations. In principle many combinations of two events can be used for determining the walking speed. The best suitable combinations are those for which almost always the same path is followed and whereby the person bridges the distance between the locations without stops to perform other activities.

A very suitable path for determining information about the walking speed is a path 19 (FIG. 2) between a door 13 of the toilet 6 and the door 17 of the living room 3. This path 19 is often used when visiting the toilet 6. Usually the person is walking directly to the living room and will seldom make a detour. In principle also the path in the other direction, from living room 3 to the toilet 6, can be used. However the path in the direction from toilet to living room is preferred. This is because typical motion sensors (located in the living room 3) are faster (more accurate) in signaling motion than in signaling absence of motion.

The program has a routine for detecting a sequence of event E6, indicating that the person is leaving the toilet 6, followed by event E2 indicating that the person has entered the living room through the door 17 and determining a travel time (tt), which is equal to the time difference between the detection of the two subsequent events E6 and E2.

Figure 3:
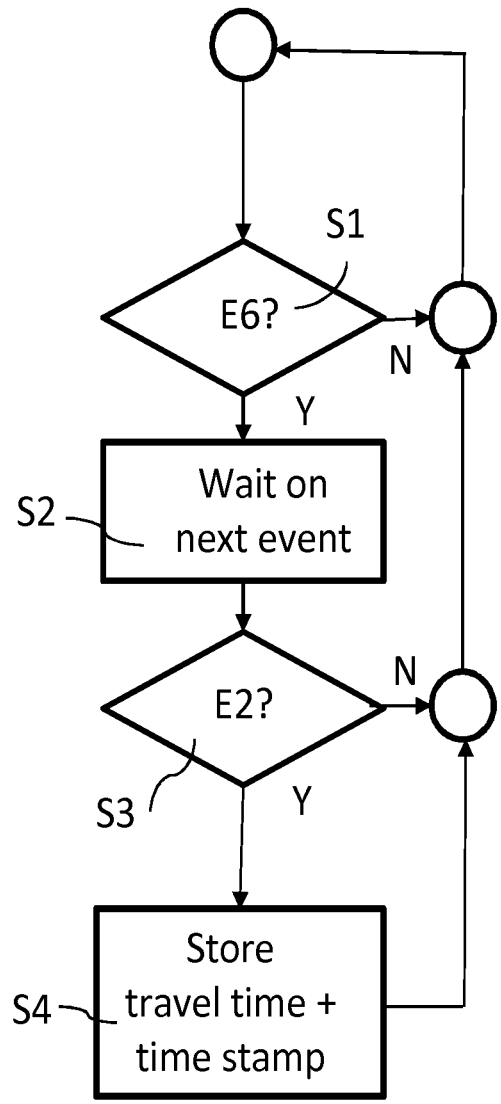
FIG. 3 shows a flow diagram of an exemplary program for determining the walking speed for use in an embodiment of the system according to the invention.

FIG. 3 shows a flow diagram of an exemplary program for determining the walking speed. In a loop comprising step S1 it is continuously checked whether event E6 occurs. If so, then a waiting step S2 is executed. In step S2 a timer is started and a wait loop is performed until a next event is detected. In Step S3 it is checked whether the next detected event is event E2. If not, then the program jumps to step S1. If the detected next event was event E2 then in step S4 the timer value is determined. This value is the travel time (tt), indicating the time difference between event E2 and event E6. The travel times (tt) are stored in a list in the data memory 26. Subsequently the program jumps to step S1 again.

Several formats are possible for the list with travel times (tt). In a simple format the travel times (tt) are stored in the list in the order in which the travel times (tt) are determined.

With this format a change in travel speed can be derived by comparing travel times (tt) which are recently placed in the list with travel times (tt) which are earlier placed in the list.

FIG. 4 shows another possible format for the list, indicated by reference sign 45. The list 45 in FIG. 4 comprises 4 columns. The dates and times at which the travel times (tt) are determined are stored in column 40 and 41 respectively. The corresponding travel times (tt) are stored in column 42.

Column 43 comprises a reliability indicator RI which indicates whether the determined travel time (tt) is reliable.

For several reasons the determined travel time (tt) may be unreliable. This will for example be the case in case the person does not walk directly from the toilet 6 to the living room, but enters the bedroom before he goes to the living room 3. This will result in a travel time (tt) which is substantially longer than usual. Row 44 in the list shows a typical value of a travel time (tt) for the situation that the person did not directly walk from the toilet 6 to the living room. The determined travel time (tt) has a value of 27 seconds which is substantially higher that the other values of the travel times (tt) determined in the last period. So by checking whether the determined travel time (tt) is substantially different from the other walking times determined in the same period it can be determined whether the travel time (tt) is reliable or not. This can for example be done by determining the average travel time (tt) of a day and declare all travel times (tt) which are a certain threshold (th 1) higher than the average as unreliable. The threshold (th1) is chosen such that only or almost only travel times (tt) pass the reliability test which correspond with an uninterrupted walk along the path 19.

The determined travel times (tt) are also unreliable in case another person is visiting the home. This may cause measurements of travel times (tt) for other persons than the monitored person. Moreover it is not sure whether the subsequent events E6 and E2 used for the measurement of the travel times (tt) are caused by the same person. This might lead to very short travel times (tt) measurements. Such very short times (much lower than average) must be marked unreliable. In the system according to the invention an indication of the likelihood that another person was visiting the living space 20 is determined for an observation period in which travel times (tt) are determined. In case in such observation period it is determined that likely another person was visiting the living space 20, all determined travel times (tt) in that observation period are declared unreliable. There exist several possibilities to determine the likelihood of the presence of a visitor, for example by using several presence sensors and detecting whether at the same time more than one person is present in the living space 20.

Cameras can be used in combination with image analyzing technology to detect more than one person in the images captured by the cameras.

Another possibility is to detect events which occur within such a short time from each other that it is impossible that they are caused by the same person.

A very simple, cost effective method is the detection of the number of events that occurs in the certain observation period and comparing this number with a reference indicating the usual number of events that is detected in corresponding observation periods. If in the observation period the detected number is substantial higher than the reference this is an indication of the presence of a visitor. In that case all determined travel times (tt) for that observation period are declared unreliable. A period of 24 hours is very suitable, because the activities of a person are in general the same per day.

Figure 5:
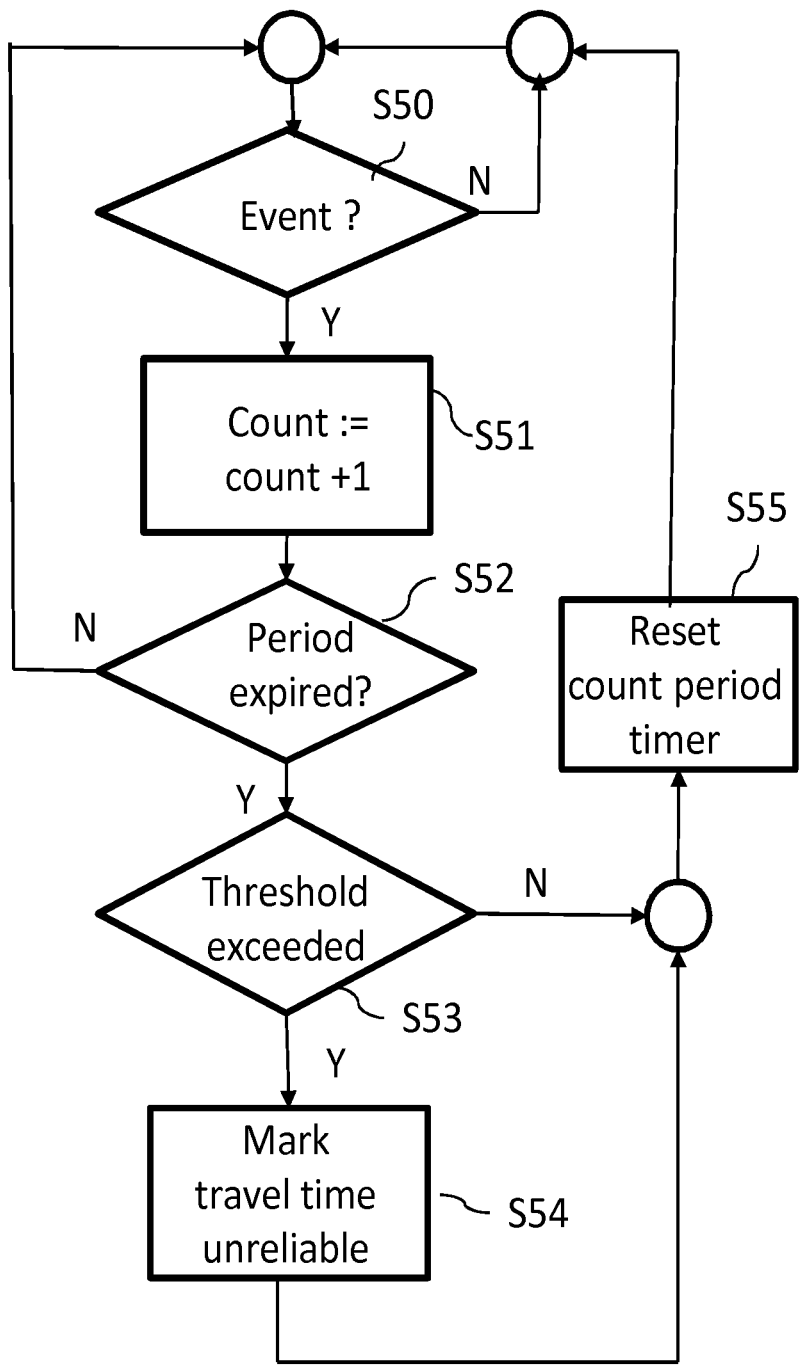
FIG. 5 shows a flow diagram of an exemplary program routine for determining the likelihood that a further person is in the living space for use in an embodiment of the system according to the invention.

A flow diagram of an exemplary program routine for determining the likelihood in this manner is shown in FIG. 5. In step S50 it is continuously checked whether an event occurs. If so then an event counter is incremented in step S51. Step S51 is followed by step S52 in which it is detected whether the observation period has expired. If not, then step S52 is followed by step S50. In case in step S52 an expiration of the observation period is determined, then in step S53 it is checked whether the number of events is substantial higher than the reference by comparing this number with a threshold value (th2). This threshold value (th2) can be a fixed value, but preferably this threshold is related to the average number of events in the observation period, for example 130% of the average value. If the threshold value (th2) is not exceeded step S55 is executed in which the event counter is reset and a jump to step S50 is made. If the threshold value is exceeded then in step S54 all travel times (tt) determined in the corresponding period are declared unreliable and the reliable indicator R1 is set. In the list of FIG. 4 this is done for the travel times (tt) determined on Mar. 7, 2014. After the executing of step S54 the program continues with step S55.

In case the travel times (tt) are stored together with the moment that the travel time (tt) is determined, change in travel time (tt) can be determined by comparing travel times (tt) determined at earlier moments. This can for example be done by comparing the average travel time (tt) of last week with the average travel time (tt) a number of weeks earlier, for example 8 weeks earlier. It will be clear that several other methods can be used to determine a change in travel speed. For example by comparing the average of the last week with the average for the last 3 months. In case the walking speed is decreased substantially such that it indicates a declining health or illness, this can be reported to a caregiver or a family member of the monitored person.

Hereinbefore the change is determined by comparing an average of recent travel times (tt) with the average of travel times (tt) determined earlier. It will be clear for the skilled man that instead of the average of recently determined travel times, also one recently determined travel time (tt) can be used in the comparison. This can be for example the median of values of a sequence of recently determined travel times (tt) or another recently determined travel time (tt).

Figure 6:
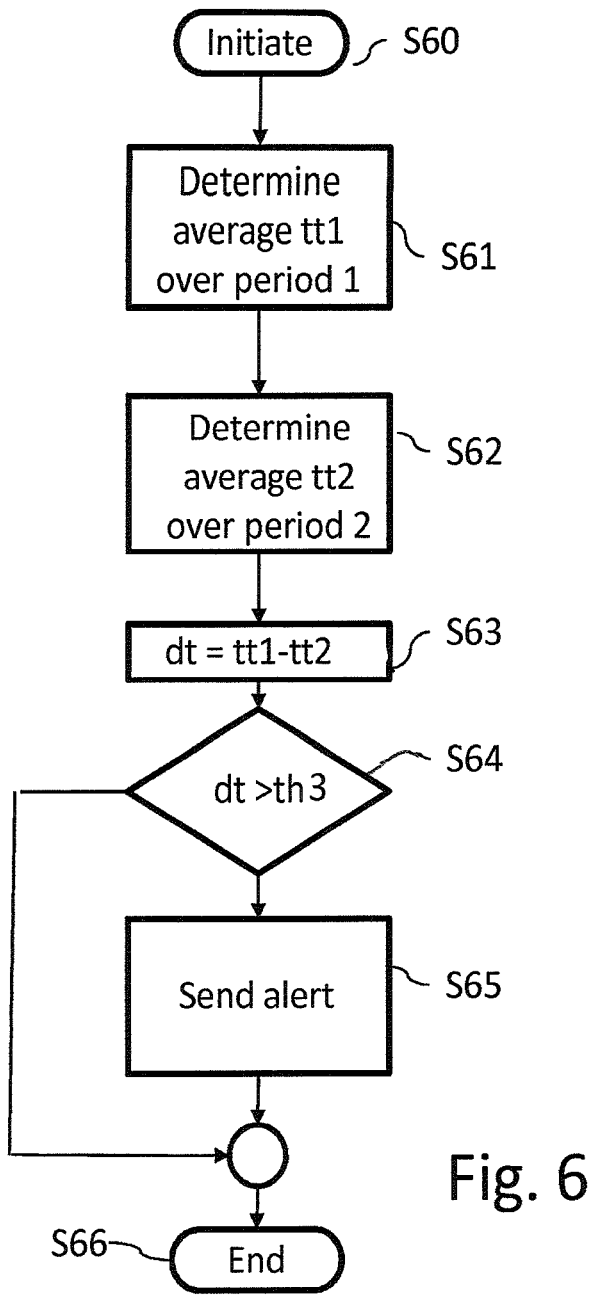
FIG. 6 shows a diagram of an embodiment of a program for determining the change in the walking in travel time over time for use in an embodiment of the system according to the invention.

FIG. 6 shows a flow diagram of an embodiment of a program for determining the change in the walking in travel time (tt) over time. This program is periodically executed, for example with a frequency of one execution per day. The program starts with an initiating step S60. After step S61 is executed. In this step the average travel time (tt) for a recent period in the near past is determined. This recent period can for example be the 7 days directly preceding the start of the program. The calculation of the average is done on the bases of the data in the list with travel times (tt) stored in the data memory 26.

After step S61 step S62 is executed in which the average travel time (tt) for period 2 located before the recent period 1 is calculated on the basis of the list of travel times. Period 2 can for example be a 7 day period located a number of days before the recent period 1. Subsequently the average travel times (tt) for recent period 1 and the average travel time (tt) for period 2 are compared in step S63. A difference (dt) between these average indicates a changing in walking speed. In step S64 it is detected whether the difference dt exceeds a threshold value (th3), indicating a serious decrease of the walking speed. If so then an alert message is sent to a caregiver or family member via the smartphone app 106 in step S65. It is also possible to report the actual change periodically, so that the caregiver or family member has a good view on the development of the walking speed and indirectly a good view on the development of the health of the monitored person. If no in step S64, or at the end of step S65, the program ends in step S66.

It will be clear that alert messages can be sent via other communication channels, for example to a so-called tablet computer connected to the internet 25.

In the embodiments described above the software module is incorporated in an internet server. However it will be clear for the skilled man that this software can also be incorporated in a central unit located in the living space 20.

Figure 7:
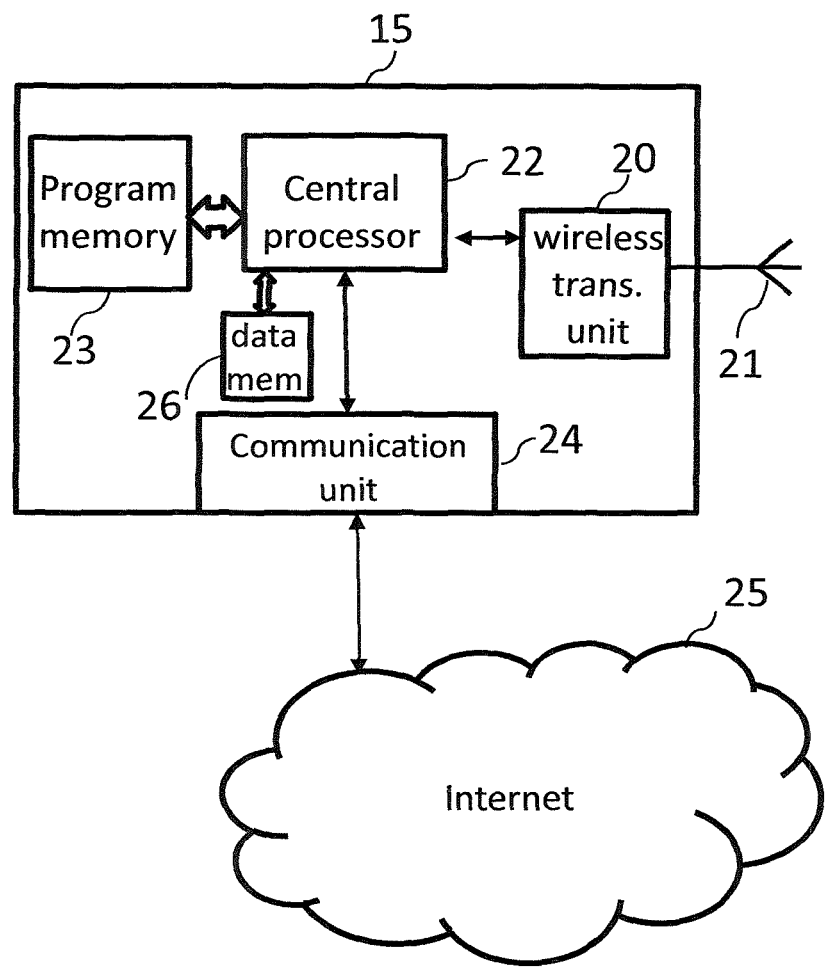
FIG. 7 shows an embodiment of the central unit 15 for use in an embodiment of the system according to the invention.

FIG. 7 shows an embodiment of a suitable central unit 15. The central unit 15 comprises a program-controlled processor 22. Processor 22 is of usual type which can execute program instructions of a computer program loaded in a program memory 23. The processor 22 is coupled with a wireless transmission unit 20 for the wireless communication with the sensors 8, 9 10 and 11 via an antenna 21. The processor 22 is further coupled with an Internet communication unit 24 enabling communication to the outside world via the Internet 25. The central unit 15 is further provided with a data memory 26 for storing information derived during the execution of the computer program in the program memory 23.

It will be appreciated by those skilled in the art that the methods and algorithms described hereinabove may be utilized to see if the monitored person's walking speed has increased. For example, it may be expected that a medication taken by the person would improve the health of the resident. This improvement may be manifested by an increase in the monitored person's walking speed over a period of time, which would result in shorter travel times. For example, if the monitored person is recovering from a bypass surgery, the recovery may be manifested by an improved walking speed of the monitored person. The methods and algorithms described hereinabove may be utilized to monitor the improvement in walking speed and therefore the progress in recovery over a number of days, weeks or months. Thus, such statistical walking speed data may be used as a prognostic tool.

It will be appreciated by those skilled in the art that the methods and algorithms described hereinabove may be embedded in a dedicated processor such as an ASIC (application specific integrated circuit) or, a digital signal processor configured for processing the signals.

While the invention has been described in detail in connection with only a limited number of embodiments, it should be readily understood that the invention is not limited to such disclosed embodiments. Rather, the invention can be modified to incorporate any number of variations, alterations, substitutions or equivalent arrangements not heretofore described, but which are commensurate with the spirit and scope of the invention. Additionally, while various embodiments of the invention have been described, it is to be understood that aspects of the invention may include only some of the described embodiments. Accordingly, the invention is not to be seen as limited by the foregoing description, but is only limited by the scope of the appended claims.

What is claimed is:

1. A system for identifying a change in walking speed of a person, the system comprising:
   a plurality of sensors disposed among a plurality of locations in a living space, wherein each of the plurality of sensors is operable to detect one of motion and location of the person, and
   a processor coupled to the sensors for:
      determining a travel time for a path traveled by the person through the living space based on signals output by the plurality of sensors and to store the travel time,
      determining a reliability indication of the likelihood that another person is visiting the living space, and
      identifying a change in the person's walking speed by identifying changes in the travel time for the path traveled by the person through the living space, disregarding travel times which are indicated as unreliable by the reliability indication.

2. The system as claimed in claim 1 wherein the processor is operable to determine the occurrence of events from at least one of the following:
   the signals received from said sensors,
   additional signals received from additional sensors detecting a presence of each of said persons in the living space, and
   activities of each of said persons in the living space, which events are indicative of activities caused by each of said persons in the living space, wherein a number of events is determined in an observation period, wherein the reliability indication for the observation period is dependent on the number of events determined in the observation period.

3. The system as claimed in claim 2, wherein the observation period has a predetermined length, and wherein the processor is operable to count the number of events that are detected in the observation period and to exclude the determined travel times in the observation period wherein this count exceeds a threshold value.

4. The system as claimed in claim 3, wherein the system is configured to indicate the determined travel time as unreliable in case the determined travel time is larger than a first threshold or smaller than a second threshold.

5. The system as claimed in claim 1 wherein said sensors include only two sensors used for determining the travel times.

6. The system as claimed in claim 5, wherein a first one of the two sensors is a sensor for detecting the presence of the person in one of a bathroom and toilet, and a second one of the two sensors is a sensor for detecting the presence of the person in another room.

7. The system as claimed in claim 1, wherein the processor is operable to compare at least one current travel time with a reference travel time to determine if travel times are changing over time.

8. The system as claimed in claim 7, wherein the processor is operable to determine the reference travel time as an average travel time in a preceding period.

9. The system as recited in claim 1, wherein the system is configured to send an alert to a caregiver when the system determines that the travel times are changing over time.

10. A non-transitory computer-readable medium, comprising: programming instructions stored in the medium, for use in the system according to claim 9.

11. The system according to claim 1 wherein the processor includes a programmable processor and the system further includes a memory loaded with a computer program with programming instructions enabling the processor to perform the aforementioned steps of determining the travel time, determining the reliability indication and identifying the change in walking speed.

\* \* \* \* \*